US008518260B2

(12) United States Patent
Raimann et al.

(10) Patent No.: US 8,518,260 B2
(45) Date of Patent: Aug. 27, 2013

(54) METHOD OF CONTROLLING DIFFUSIVE SODIUM TRANSPORT IN DIALYSIS

(75) Inventors: Jochen G. Raimann, New York, NY (US); Erik Lars Penne, Amsterdam (NL); Stephan Thijssen, New York, NY (US); Peter Kotanko, New York, NY (US); Nathan W. Levin, New York, NY (US)

(73) Assignee: Fresenius Medical Care Holdings, Inc., Waltham, MA (US)

(*) Notice: Subject to any disclaimer, the term of this patent is extended or adjusted under 35 U.S.C. 154(b) by 194 days.

(21) Appl. No.: 12/896,009

(22) Filed: Oct. 1, 2010

(65) Prior Publication Data

US 2011/0079558 A1   Apr. 7, 2011

Related U.S. Application Data

(60) Provisional application No. 61/277,957, filed on Oct. 1, 2009.

(51) Int. Cl.
  *B01D 61/32* (2006.01)
  *B01D 61/24* (2006.01)
  *B01D 61/30* (2006.01)
(52) U.S. Cl.
  USPC ........... 210/647; 210/645; 210/646; 210/739; 604/4.01; 604/5.04; 604/28
(58) Field of Classification Search
  USPC .................... 210/645, 646, 647, 739, 746, 85, 210/86, 97, 103, 134, 143; 604/4.01, 5.01, 604/5.04, 28, 29
  See application file for complete search history.

(56) References Cited

U.S. PATENT DOCUMENTS 5,091,094 A * 2/1992 Veech ........................... 210/647

OTHER PUBLICATIONS

Cheung, A. K., et al., "Seasonal Variations in Clinical and Laboratory Variables Among Chronic Hemodialysis Patients," *J. Am Soc. Nephrol* 13: 2345-2352 (2002).
Li, Szu-Yuan, et al., "Seasonal Variations in Serum Sodium Levels and Other Biochemical Parameters Among Peritoneal Dialysis Patients," *Nephrol Dial Transplant* 23:687-692 (2008).
DePaula, F.M. et al., "Clinical consequences of an individualized dialysate sodium prescription in hemodialysis patients", *Kidney International*, 66:1232-1238, 2004.
Keen, M.L., and Gotch, F.A., "The Association of the Sodium "setpoint" to Interdialytic Weight Gain and Blood Pressure in Hemodialysis Patients," The International Journal of Artificial Organs, 30(11):971-979 (2007).
Murisasco, A., et al., "Sequential Sodium Therapy Allows Correction of Sodium-Volume Balance and Reduces Morbidity," Clinical Nephrology, 24(4): 201-208 (1985).
Gotch, F.A., et al., "Preliminary Clinical Results with Sodium-Volume Modeling of Hemodialysis Therapy," Proc. Dialysis Transplant Forum, (1980).

* cited by examiner

*Primary Examiner* — John Kim
(74) *Attorney, Agent, or Firm* — Hamilton, Brook, Smith & Reynolds, P.C.

(57) ABSTRACT

A method of controlling diffusive sodium transport from the dialysate solution to the blood of a patient undergoing hemodialysis treatment or from the blood to the dialysate solution includes calculating $SNa^+_{average}$, an average of the patient's historic serum sodium concentrations, and estimating $SNa^+_{estimated}$, the patient's pre-dialysis serum sodium concentration, based on the average of the patient's measured historic pre-dialysis serum sodium concentrations, $SNa^+_{measured}$. The method enables adjusting $DNa^+$, the sodium concentration of the dialysate solution, based on the average of the patient's historic serum sodium concentrations, $SNa^+_{average}$, if needed, and performing the dialysis treatment of the patient using a dialysate solution containing a sodium concentration $DNa^+$.

4 Claims, 8 Drawing Sheets

METHOD OF CONTROLLING DIFFUSIVE SODIUM TRANSPORT IN DIALYSIS

RELATED APPLICATION

This application claims the benefit of U.S. Provisional Application No. 61/277,957, filed on Oct. 1, 2009. The entire teachings of the above application are incorporated herein by reference.

BACKGROUND OF THE INVENTION

The pre-dialysis serum sodium ($Na^+$) concentration is relatively constant in hemodialysis patients, but varies with each patient's individual osmolar set point. See F. M. De Paula, et al., *Clinical consequences of an individualized dialysate sodium prescription in hemodialysis patients*, Kidney International, Vol. 66 (2004) pp. 1232-1238; A. S. Peixoto, et al., *Long-Term Stability of Serum Sodium in Hemodialysis Patients*, Blood Purification, Vol. 29 (2010) pp. 264-267, and M. L. Keen, and F. A. Gatch, *The association of the sodium "setpoint" to interdialytic weight gain and blood pressure in hemodialysis patients*, The International Journal of Artificial Organs, Vol. (11) pp. 971-979 (2007). The gradient ($GNa^+$) between the serum sodium ($SNa^+$) concentration and the dialysate sodium ($DNa^+$) concentration is a major determinant of post-dialytic $SNa^+$ concentration. A positive gradient ($DNa^+>SNa^+$) can result in a higher post-dialytic $SNa^+$, and consequent thirst, excess interdialytic weight gain, volume overload, and increased blood pressure. A negative gradient ($DNa^+<SNa^+<$) is also undesirable because it can result in the patient becoming hypotensive. Basing $DNa^+$ on $SNa^+$ (e.g., gradient $GNa^+=0$) would minimize diffusive sodium transport, and thus reduce the aforementioned problems. However, the measurement of the serum sodium concentration, $SNa^+_{measured}$, of each patient before each dialysis treatment is costly and time consuming using existing technology.

Therefore, there is a need for a method of controlling diffusive sodium transport from the dialysate solution to the blood of a patient undergoing dialysis treatment that minimizes or eliminates the aforementioned problems.

SUMMARY OF THE INVENTION

The invention is generally related to a method of controlling diffusive sodium transport from the dialysate solution to the blood of a patient undergoing hemodialysis treatment or from the blood to the dialysate solution. The method includes calculating $SNa^+_{average}$, an average of the patient's historic serum sodium concentrations, and estimating $SNa^+_{estimated}$, the patient's pre-dialysis serum sodium concentration, based on the average of the patient's historic pre-dialysis serum sodium concentrations, $SNa^+_{measured}$. The method enables adjusting $DNa^+$, the sodium concentration of the dialysate solution, based on the average of the patient's historic serum sodium concentrations, $SNa^+_{average}$, if needed, and performing the dialysis treatment of the patient using a dialysate solution containing a sodium concentration $DNa^+$.

In some embodiments, the patient's present pre-dialysis serum sodium concentration is estimated as equal to the average of the patient's historic serum sodium concentrations measured pre-dialysis treatment over a historic time interval. The patient's measured historic serum sodium concentrations can be corrected for void volume and/or the Gibbs-Donnan effect. In certain embodiments, the sodium concentration of the dialysate solution, $DNa^+$, is equal to the estimated pre-dialysis serum sodium concentration, $SNa^+_{estimated}$. In some embodiments, the historic time interval is at least 2 months. In other embodiments, the historic time interval is at least 4 months.

This invention provides a method of accurately predicting a dialysis patient's pre-dialysis serum sodium concentration, $SNa^+_{estimated}$, which in turn, allows a dialysis solution to be used for dialysis of the patient with a dialysate sodium concentration, $DNa^+$, based upon the patient's $SNa^+_{estimated}$. Use of such a dialysate solution reduces the health consequences of a positive or negative sodium gradient, $GNa^+$, during dialysis.

This invention has many advantages, including the ability to eliminate the measurement of the serum sodium concentration, $SNa^+_{measured}$, of each patient before each dialysis treatment.

BRIEF DESCRIPTION OF THE DRAWINGS

The foregoing will be apparent from the following more particular description of example embodiments of the invention, as illustrated in the accompanying drawings illustrating embodiments of the present invention.

DETAILED DESCRIPTION OF THE INVENTION

The method of controlling diffusive sodium transport from the dialysate solution to the blood of a patient undergoing hemodialysis treatment or from the blood to the dialysate solution includes calculating $SNa^+_{average}$, an average of the patient's historic serum sodium concentrations, and estimating $SNa^+_{estimated}$, the patient's pre-dialysis serum sodium concentration, based on the average of the patient's historic pre-dialysis serum sodium concentrations, $SNa^+_{measured}$, measured pre-dialysis treatment over a historic time interval. The pre-dialysis serum sodium concentration of a patient can either be measured with flame photometry, or with an ion selective electrode using either direct (undiluted specimens) or indirect (diluted specimens) potentiometry. The results obtained by indirect potentiometry can be corrected for void volume and the Gibbs-Donnan effect, as discussed below. Alignment was shown to reduce consequences of positive or negative gradients. See F. M. De Paula, et al., *Clinical consequences of an individualized dialysate sodium prescription in hemodialysis patients*, Kidney International, Vol. 66 (2004) pp. 1232-1238. In clinical routine of the treatment of chronic hemodialysis patients, the measurement of serum sodium, $SNa^+_{measured}$, is taken pre-dialysis, typically once a month, preferably in the first week of every month, more preferably mid-week during the first week of every month of a thrice weekly dialysis treatment regimen. The data is accumulated over a historic time interval that is preferably at least 2 months, more preferably at least 4 months. A particularly preferred historic time interval is at least 4 months, but not more than 12 months.

The estimate of the patient's pre-dialysis serum sodium concentration, $SNa^+_{estimated}$, is based on the arithmetic average of the patient's historic pre-dialysis serum sodium concentrations, $SNa^+_{measured}$. In some embodiments, the patient's pre-dialysis serum sodium concentration is estimated as equal to the average of the patient's historic serum sodium concentrations measured pre-dialysis treatment over the historic time interval. The patient's measured historic serum sodium concentrations can include corrections for void volume and the Gibbs-Donnan effect discussed below. A patient's normal pre-dialysis serum sodium concentration typically varies from about 135 mmol/liter to about 145 mmol/liter, depending on each patient's individual osmolar set point. See M. L. Keen, and F. A. Gotch, *The association of the sodium "setpoint" to interdialytic weight gain and blood pressure in hemodialysis patients*, The International Journal of Artificial Organs, Vol. 30 (11) pp. 971-979 (2007).

It was found that the correlation of the measured serum sodium $SNa^+_{measured}$ of Month(i=0) with the measured serum sodium $SNa^+_{measured}$ of the preceding month (Month(i=−1), was poor ($R^2$=0.29). The model employing the average over the preceding 12 months resulted in a better correlation than a model over the preceding 4 months, which was in turn better than a model employing an average over the preceding 2 months. It is expected that a model employing an average over a historic time interval larger than 12 months would show a worse correlation, due to, for example, possible significantly increased deterioration of the patient's health during a period closer to the dialysis treatment.

The method enables adjusting $DNa^+$, the sodium concentration of the dialysate solution, if needed, based on either $SNa^+_{average}$ or $S'Na^+_{average}$, the average of the patient's historic measured serum sodium concentrations, $SNa^+_{measured}$ or $S'Na^+_{measured}$ (the ' refers to $SNa^+$ estimates taking the void volume correction and the Gibbs-Donnan effect into account, as discussed below). By contrast, in a typical dialysis treatment using a dialysate with an unadjusted sodium concentration, that concentration is typically set at about 138 to 142 mmol/liter. Controlling diffusive sodium transport from the dialysate solution to the blood of a patient undergoing dialysis treatment or from the blood to the dialysate solution can include adjusting $DNa^+$ to be slightly smaller than the serum sodium concentration, such that a physician-prescribed slight diffusive loss of sodium from the patient's blood is accomplished, for example, for treatment of hypertensive patients. Additionally, controlling diffusive sodium transport from dialysate solution to blood of a patient undergoing dialysis treatment or from the blood to the dialysate solution can include adjusting $DNa^+$ to be slightly larger than the serum sodium concentration, such that a physician-prescribed slight diffusive gain of sodium by the patient's blood is accomplished, for example, for treatment of hypotensive patients. See A. Murisasco, G. France, G. Leblond, C. Durand, M. El Mehdi, A. Crevat, R. Elsen, Y. Boobes, and M. Baz, *Sequential sodium therapy allows correction of sodium-volume balance and reduces morbidity*, Clinical Nephrology, Vol. 24 (4) pp. 201-208 (1985).

In certain embodiments, the sodium concentration of the dialysate solution, $DNa^+$, is set equal to the estimated pre-dialysis serum sodium concentration, either $SNa^+_{estimated}$ or $S'Na^+_{estimated}$, which is based on either $SNa^+_{average}$ or $S'Na^+_{average}$ the average of the measured historic serum sodium concentrations, $SNa^+_{measured}$ and $S'Na^+_{measured}$, respectively. Additionally, the sodium concentration of the dialysate solution, $DNa^+$, should be adjusted to account for two additional factors: firstly, the void volume correction and secondly, the Gibbs-Donnan effect. The former requires the distinction between plasma (containing plasma water, lipid and proteins) and plasma water. Void volume correction is only required for measurements by indirect potentiometry (measuring the serum sodium concentration in a defined amount of plasma and thus creating the need for void volume correction); indirect potentiometry can produce lower results, as compared to direct potentiometry and flame photometry (the former directly measuring conductivity and thus electrically active sodium in plasma water and the latter measuring the total amount of sodium in a defined volume). This distinction is necessary because the sodium concentration in the plasma water is the concentration determining the diffusive processes at the dialysis membrane. Secondly, the Gibbs-Donnan effect, which is caused by negative protein charges (on the blood side), impacts the transmembrane flux of (positively charged) sodium ions, and therefore also has to be taken into account for alignment.

The following empirical equation was proposed by Gotch et al. (1980) to calculate plasma water sodium concentration (PWNa$^+$) by accounting for the void volume:

$$PWNa^+ = \frac{SNa^+}{0.989 - 0.0047 \times TP}, \quad (1)$$

where SNa$^+$ is the serum sodium concentration determined by indirect potentiometry and TP is the total protein concentration in the plasma.

The following empirical equation was proposed by Gotch et al. (1980) to account for the Gibbs-Donnan effect:

$$\text{Donnan-coefficient} = 1.007 - 0.009 \times TP \quad (2)$$

where TP is the total protein concentration.
The equation accounting for both effects is $$S'Na^+ = SNa^+ \times \frac{1.007 - 0.009 \times TP}{0.989 - 0.0047 \times TP}, \quad (3)$$

where S'Na$^+$ is the sodium concentration which results in a dialysate to serum sodium gradient of zero (GNa$^+$=0) taking the void volume and the Gibbs-Donnan effect into account, SNa$^+$ is the serum sodium concentration (either estimated or measured, but measured with indirect potentiometry) and TP is the total protein concentration in the plasma.

See F. A. Gotch, M. A. Lam, M. Prowitt, and M. L. Keen, *Preliminary Clinical Results with Sodium-Volume Modeling of Hemodialysis Therapy*, Proceedings Clinical Dialysis Transplant Forum, Vol, 10 (1980) pp. 12-17.

Exemplification

The predictability of the next month's serum sodium concentration, SNa$^+_{estimated}$ and S'Na$^+_{estimated}$, respectively, on the basis of the patient's historic serum sodium concentrations, SNa$^+_{measured}$ and S'Na$^+_{measured}$, measured pre-dialysis treatment over a historic time interval was investigated. In this retrospective analysis, monthly serum sodium concentrations, SNa$^+_{measured}$ and S'Na$^+_{measured}$, were analyzed over one year (12 months) in a large group of chronic maintenance hemodialysis patients receiving dialysis at Renal Research Institute clinics. Linear regression analysis was employed to investigate the relationship between SNa$^+_{measured}$ in Month (i=0) and SNa$^+_{average}$, the arithmetic average of Months (i=−4) to (i=−1).

Figure 1:
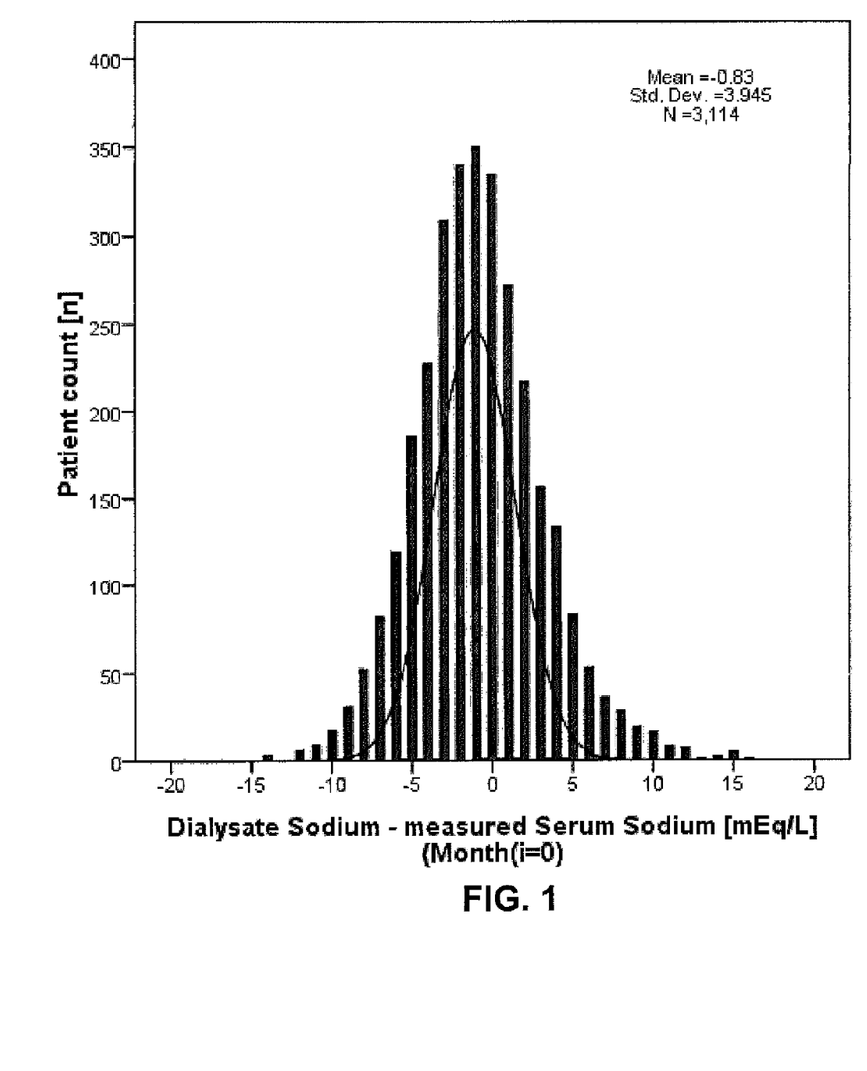
FIG. 1 is a graph of the number of patients for a large group of hemodialysis patients studied, where $SNa^+_{measured}$ as well as $DNa^+$ were available (n=3,114), versus the distribution of the dialysate to serum sodium gradient $GNa^+$ ($GNa^+=DNa^+-SNa^+_{measured}$). A normal distribution curve approximation, based on the average and the standard deviation of the data, is indicated by a solid line.
Figure 2:
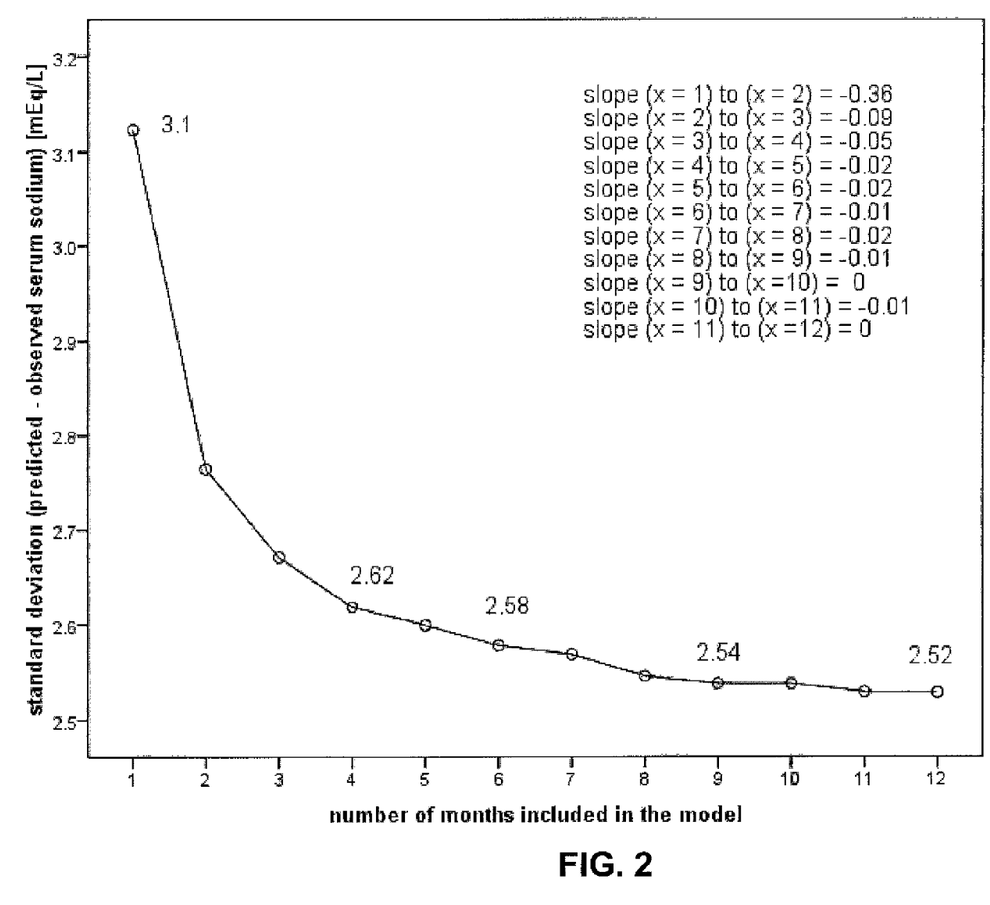
FIG. 2 is a graph showing the standard deviation of the difference between the average serum sodium over a certain period of time, $SNa^+_{average}$, of different tested models, and measured serum sodium concentrations, $SNa^+_{measured}$, versus the number of months used for the calculation of the average serum sodium concentration, $SNa^+_{average}$.
Figure 3:
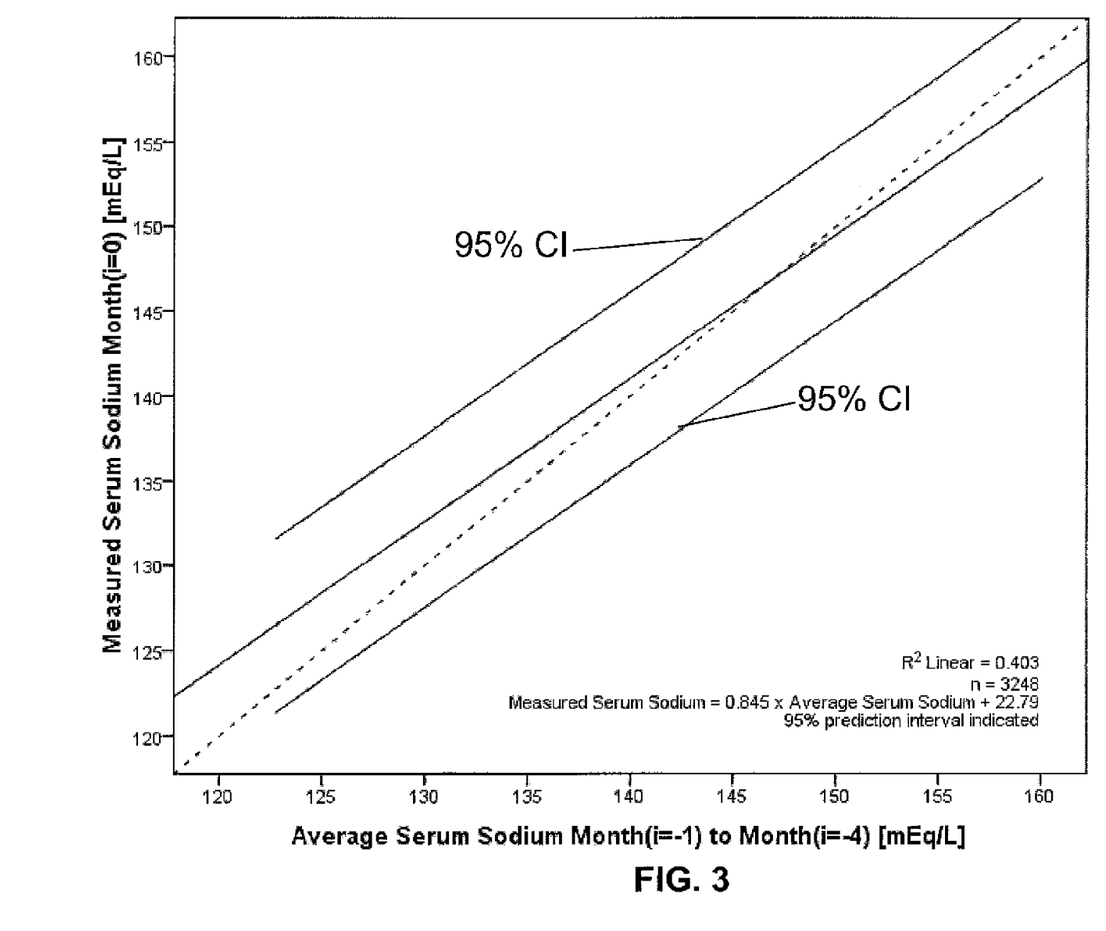
FIG. 3 is a graph of the serum sodium concentration measured in the current month $SNa^+_{measured}$ Month(i=0) versus the average serum sodium concentration $SNa^+_{average}$ averaged over the previous 4 months ($SNa^+_{measured}$(Month(i=−1) to Month(i=4)). A line of indentity is indicated by a dashed line.

Monthly SNa$^+_{measured}$ as well as DNa$^+$ values of 3,114 hemodialysis patients were available (1,763 males, 1,755 blacks, mean age 60 years). The SNa$^+_{measured}$ Month(i=0) was 140.4±3.4 mmol/liter. As illustrated in FIG. 1, GNa$^+$ in Month(i=0) was −0.83±3.95 mmol/liter (95% confidence interval (CI)-0.97 to −0.70). SNa$^+_{measured}$ Month(i=0) and SNa$^+_{measured}$ Month(i=−1) were poorly correlated (R$^2$=0.29). As illustrated in FIG. 2, various models were tested, including an increasing amount of monthly SNa$^+_{measured}$ values, and the arithmetic average SNa$^+_{measured}$ of Months(i=−1) to (i=−4) was preferred. After 4 months the slope decreases below −0.05 and flattens consecutively, which indicates no substantial gain for the estimation of SNa$^+_{estimated}$. The correlation of the average serum sodium concentration of this preferable observation period (i.e., historic time interval) SNa$^+_{average}$ Months(i=−1 to −4) to SNa$^+_{measured}$ Month(i=0) is illustrated in FIG. 3 (SNa$^+_{measured}$ Month(i=0)=22.79+ 0.845*SNa$^+_{average}$ Months(i=−1 to −4); R$^2$=0.40), and listed in Table 1 below. Other models using different historic time intervals are not shown.

TABLE 1

Regression coefficients$^a$ for Average of Serum Sodium Concentration (i = −1 to i = −4)

| Model | Unstandardized Coefficients | | Standardized Coefficients | T | Sig. | 95% Confidence Interval for B | |
|---|---|---|---|---|---|---|---|
| | B | Std. Error | Beta | | | Lower Bound | Upper Bound |
| 1 (Constant) | 22.793 | 2.511 | | 9.077 | .000 | 17.87 | 27.716 |
| Average of Serum Na$^+$ Month(i = −1) to Month (i = −4) | .845 | .018 | .635 | 46.824 | .000 | .809 | .880 |

$^a$Dependent Variable: Measured Serum Na$^+$ Month (i = 0)

Figure 4:
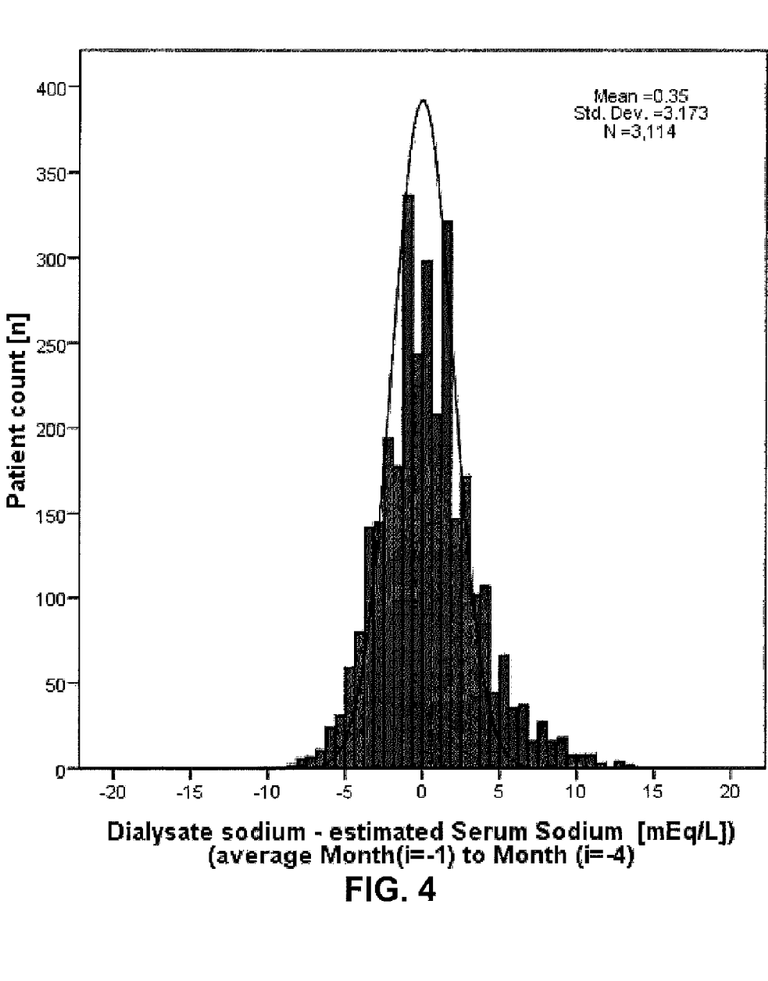
FIG. 4 is a graph of the number of patients for a large group of hemodialysis patients studied, where $SNa^+_{measured}$ as well as $DNa^+$ were available (n=3,114), versus the distribution of the dialysate to serum sodium gradient $GNa^+$ ($GNa^+=DNa^+-SNa^+_{average}$) after calculation of an average serum sodium concentration the $SNa^+_{average}$ over a historic time interval ($SNa^+_{measured}$ of Month(i=−1) to Month(i=−4)). A normal distribution curve approximation, based on the average and the standard deviation of the data, is indicated by a solid line.

As illustrated in FIG. 4, a prescription of DNa$^+$, based on the predicted SNa$^+_{estimated}$ Month(i=0) (DNa$^+$=SNa$^+_{estimated}$) using the average SNa$^+_{measured}$ over the preceding 4 months would have resulted in a GNa$^+$ (i=0) of 0.35±3.17 mmol/liter (95% CI 0.24 to 0.46), which is closer to zero than the actually observed GNa$^+$Month(i=0) of −0.83 mmol/liter.

Figure 5:
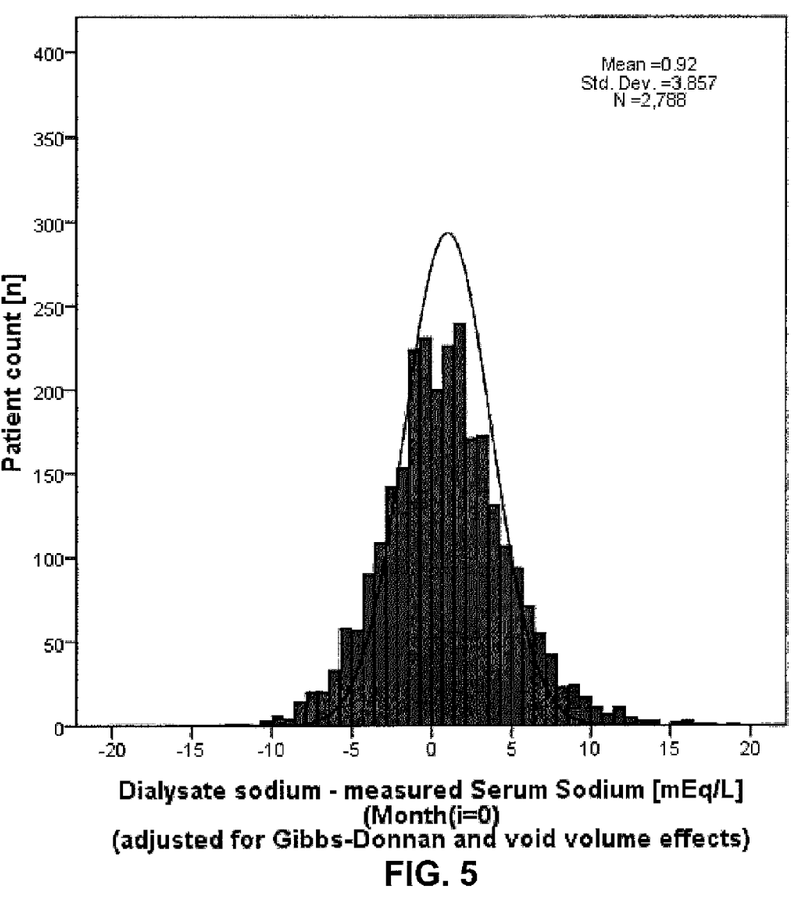
FIG. 5 is a graph of the number of patients for a large group of hemodialysis patients studied, where $SNa^+_{measured}$, $DNa^+$, and total protein concentrations (TP) were available (n=2,788), versus the distribution of the dialysate to serum sodium gradient, $G'Na^+$ ($G'Na^+=DNa^+-S'Na+_{measured}$), after adjustment for the Gibbs-Donnan effect and the void volume correction. A normal distribution curve approximation, based on the average and the standard deviation of the data, is indicated by a solid line.

As illustrated in FIG. 5 the dialysate to serum sodium gradient, G'Na$^+$, taking the Gibbs-Donnan effect and the void volume correction into account (G'Na$^+$ mm DNa$^+$-S'Na$^+_{estimated}$) in Month(i=0) was 0.92±3.86 mmol/liter (95% CI 0.77 to 1.06).

Figure 6:
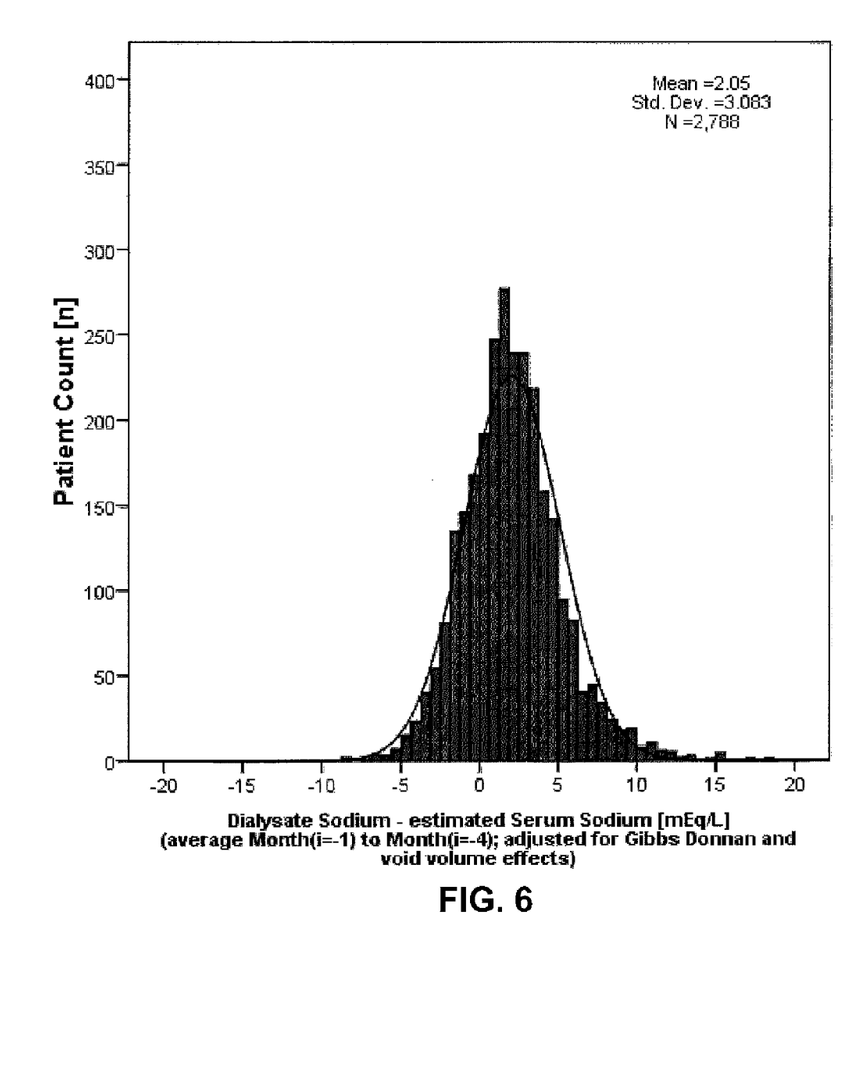
FIG. 6 is a graph of the number of patients for a large group of hemodialysis patients studied, where $SNa^+_{measured}$, $DNa^+$, and total protein concentrations (TP) were available (n=2,788), versus the distribution of the dialysate to serum sodium gradient, $G'Na^+$ ($G'Na^+=DNa^+-S'Na^+_{average}$), after adjustment for the Gibbs-Donnan effect and the void volume correction in the calculation of the average serum sodium concentration, $S'Na^+_{average}$, over a historic time interval ($S'Na^+_{measured}$ of Month(i=1) to Month(i=−4)). A normal distribution curve approximation, based on the average and the standard deviation of the data, is indicated by a solid line.

As illustrated in FIG. 6, a prescription of DNa$^+$, based on the predicted estimated Month(i=0) (DNa$^+$=S'Na$^+_{estimated}$) using the average S'Na+$_{measured}$ over the preceding 4 months would have resulted in a G'Na$^+$ (i=0) of 2.05+3.08 mmol/liter (95% CI 1.94 to 2.17).

Figure 7:
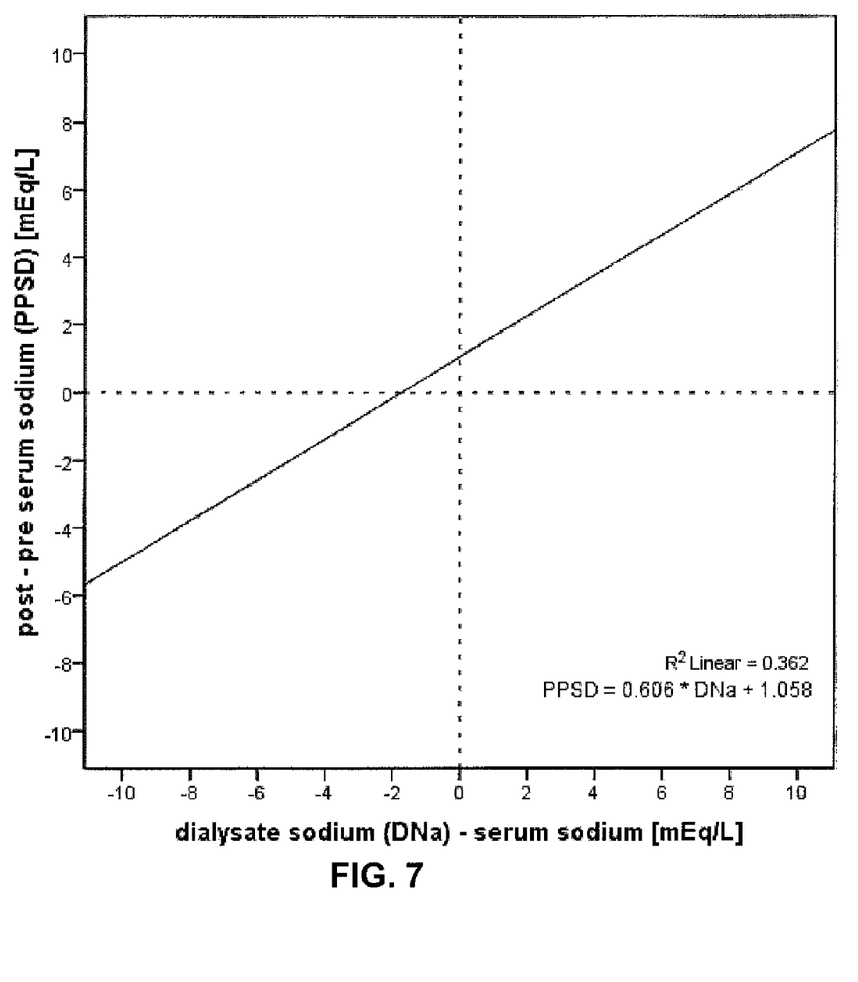
FIG. 7 is a graph of the post-dialysis minus pre-dialysis serum sodium concentration (PPSD) as a function of the nominal dialysate sodium minus serum sodium gradient.

As illustrated in FIG. 7 sodium alignment without adjusting for the void volume and the Gibbs-Donnan effect (DNa$^+$=SNa$^+$) results in an intradialytic increase of serum sodium, SNa$^+$, of approximately 1 mmol/L at a dialysate to serum sodium gradient of zero.

Figure 8:
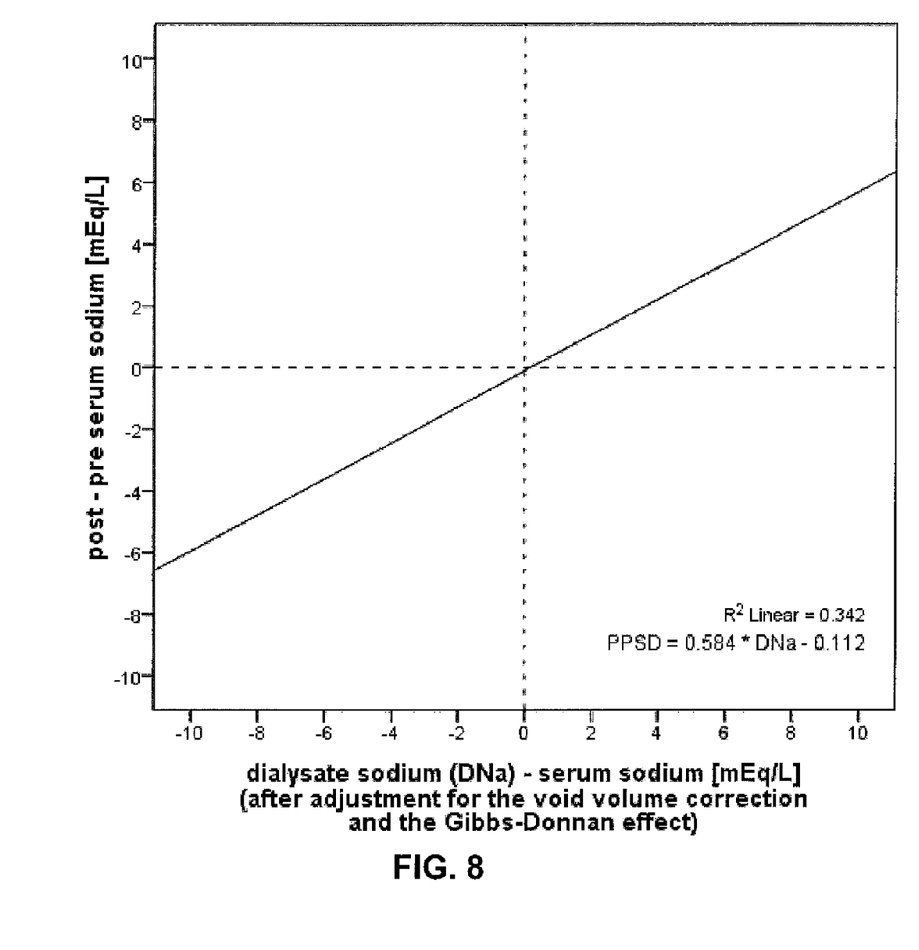
FIG. 8 is a graph of the post-dialysis minus pre-dialysis serum sodium concentration (PPSD) as a function of the dialysate sodium minus serum sodium gradient after adjustment for the void volume and the Gibbs-Donnan effect.

FIG. 8 illustrates that the intradialytic change in serum sodium, SNa$^+$, is much closer to zero (−0.112 mEq/L), following sodium alignment after adjustment for the void volume and the Gibbs-Donnan effect ($DNa^+ = S'Na^+$).

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of controlling diffusive sodium transport from dialysate solution to blood of a patient undergoing hemodialysis treatment or from blood into the dialysate solution comprising:
   a) calculating $SNa^+_{average}$, an average of the patient's measured historic serum sodium concentrations, $SNa^+_{measured}$;
   b) estimating $SNa^+_{estimated}$, the patient's pre-dialysis serum sodium concentration, based on the average, $SNa^+_{average}$, of the patient's pre-dialysis serum sodium concentrations over a historic time interval of at least 4 months;
   c) determining GNa+, a desired gradient between $SNa^+_{estimated}$ and $DNa^+$, the sodium concentration in a dialysate solution; and
   d) performing the dialysis treatment of the patient using the dialysate solution containing the sodium concentration $DNa^+$ based upon $SNa^+_{estimated}$.

2. The method of claim 1, wherein the patient's historic serum sodium concentrations include corrections for void volume and Gibbs-Donnan effect.

3. The method of claim 1, wherein $DNa^+ = SNa^+_{estimated}$.

4. The method of claim 2, wherein $DNa^+ = SNa^+_{estimated}$.

* * * * *